US012730042B2

(12) United States Patent
He et al.

(10) Patent No.: US 12,730,042 B2
(45) Date of Patent: Sep. 8, 2026

(54) TRUE TRIAXIAL DYNAMIC DISTURBANCE TEST DEVICE FOR DEEP-BURIED HARD ROCK

(71) Applicant: Northeastern University, Shenyang City (CN)

(72) Inventors: Benguo He, Shenyang City (CN); Hanyi Liu, Shenyang City (CN); Xiating Feng, Shenyang City (CN); Jiahua Guan, Shenyang City (CN); Hongyuan Fu, Shenyang City (CN); Bo Lin, Shenyang City (CN)

(73) Assignee: NORTHEASTERN UNIVERSITY, Shenyang City (CN)

( * ) Notice: Subject to any disclaimer, the term of this patent is extended or adjusted under 35 U.S.C. 154(b) by 0 days.

(21) Appl. No.: 19/122,988

(22) PCT Filed: Dec. 9, 2024

(86) PCT No.: PCT/CN2024/137749
§ 371 (c)(1),
(2) Date: Apr. 21, 2025

(87) PCT Pub. No.: WO2025/185264
PCT Pub. Date: Sep. 12, 2025

(65) Prior Publication Data

US 2026/0009705 A1 Jan. 8, 2026

(30) Foreign Application Priority Data

Mar. 8, 2024 (CN) ........................ 202410264497.1

(51) Int. Cl.
*G01N 3/02* (2006.01)
*G01N 3/08* (2006.01)
*G01N 33/24* (2006.01)

(52) U.S. Cl.
CPC ................ *G01N 3/02* (2013.01); *G01N 3/08* (2013.01); *G01N 33/24* (2013.01)

(58) Field of Classification Search
CPC .......... G01N 3/02; G01N 3/08; G01N 33/24; G01N 3/10; G01N 3/12; G01N 3/18;
(Continued)

(56) References Cited

U.S. PATENT DOCUMENTS

| | | | | |
|---|---|---|---|---|
| 7,024,922 B1 * | 4/2006 | Nakagawa | ............... | G01N 3/30 73/54.39 |
| 7,254,492 B2 * | 8/2007 | Miyamoto | ............... | G01L 5/00 73/783 |

(Continued)

FOREIGN PATENT DOCUMENTS

| | | |
|---|---|---|
| CN | 103837418 A | 6/2014 |
| CN | 103969107 A | 8/2014 |

(Continued)

OTHER PUBLICATIONS

Lei Shi et al., "Development and application of an ultra-deep drilling core geological environment true triaxial apparatus", Geotechnical Engineering Mechanics, Jul. 2023, vol. 44, No. 7, pp. 2161-2169.

*Primary Examiner* — Freddie Kirkland, III
(74) *Attorney, Agent, or Firm* — MUNCY, GEISSLER, OLDS & LOWE, P.C.

(57) ABSTRACT

A true triaxial time-dependent dynamic disturbance test device for a deep-buried hard rock includes a rigid static load loading assembly and a rigid dynamic load loading assembly. The rigid static load loading assembly applies a static load to a rock test sample, and the rigid dynamic load loading assembly applies a disturbance stress to the rock test sample. Coupled application and control of a long time-dependent static force and a disturbance stress of the rock in a true triaxial disturbance stress state are achieved. The rigid
(Continued)

dynamic load is provided with a disturbance rod in a loading direction, and a "point" disturbance mode is converted into a "face" disturbance mode through the disturbance rod, a disturbance hole and a test sample clamp, so that a disturbance mode more suitable for an actual working condition on site is provided while power consumption is reduced and time-dependent dynamic disturbance is achieved.

9 Claims, 8 Drawing Sheets

(58) Field of Classification Search
CPC .. G01N 3/32; G01N 3/04; G01N 3/06; G01N 2203/0019; G01N 2203/0075; G01N 2203/0256; G01N 2203/04; G01N 2203/0682
See application file for complete search history.

(56) References Cited

U.S. PATENT DOCUMENTS 10,324,014 B2 * 6/2019 Feng ...................... G01N 3/307
10,365,193 B2 * 7/2019 Feng ...................... G01N 3/12
10,712,252 B2 * 7/2020 Atapour ............ G01N 15/0806
11,047,782 B1 * 6/2021 Zheng ...................... G01N 3/04
11,326,995 B2 * 5/2022 Feng ...................... G01N 3/24
11,703,433 B2 * 7/2023 Zhu ...................... G01N 3/307 73/788
11,761,865 B2 * 9/2023 Liu ...................... G01N 3/12 73/788
11,982,664 B1 * 5/2024 Zheng ...................... G01N 3/10
12,055,523 B1 * 8/2024 Li ...................... G01N 3/08
12,066,424 B1 * 8/2024 Li ...................... G01N 29/223
12,210,000 B1 * 1/2025 Zhu ...................... G01N 3/08
12,292,419 B1 * 5/2025 Zhu ...................... G01N 3/08
12,411,071 B1 * 9/2025 Xia ...................... G01N 15/0826
2018/0275034 A1 * 9/2018 Feng ...................... G01N 3/307
2018/0313727 A1 * 11/2018 Feng ...................... G01N 3/12
2019/0033198 A1 * 1/2019 Atapour ............ G01N 15/0806
2021/0325287 A1 * 10/2021 Xie ...................... G01N 3/08
2022/0196527 A1 6/2022 Xiwei et al.

FOREIGN PATENT DOCUMENTS

| | | | |
|---|---|---|---|
| CN | 106289995 | A | 1/2017 |
| CN | 107036903 | A | 8/2017 |
| CN | 115201016 | A | 10/2022 |
| CN | 115655905 | A | 1/2023 |
| CN | 115683858 | A | 2/2023 |
| CN | 115931568 | A | 4/2023 |
| CN | 118090427 | A | 5/2024 |
| JP | H10206303 | A | 8/1998 |
| JP | 2015102472 | A | 6/2015 |
| KR | 20050020057 | A | 3/2005 |
| WO | WO 2016110067 | A1 | 7/2016 |
| WO | WO 2021017241 | A1 | 2/2021 |
| WO | WO 2022134187 | A1 | 6/2022 |

* cited by examiner

TRUE TRIAXIAL DYNAMIC DISTURBANCE TEST DEVICE FOR DEEP-BURIED HARD ROCK

FIELD OF THE INVENTION

The present invention relates to the technical field of a deep rock mechanical test, and in particular to a true triaxial time-dependent dynamic disturbance test device for a deep-buried hard rock.

THE PRIOR ARTS

At present, in the excavation and tunneling process of deep tunneling engineering, due to the adoption of a tunneling and blasting excavation mode of a tunnel boring machine (TBM), it is found that before being supported, a surrounding rock will be affected by a disturbance stress to be subjected to delayed rupture, which seriously threatens the life and property safety in the construction process. The scientific research direction of deep rock mechanisms has gradually changed from uniaxial and biaxial stress states to the rock physical and mechanical property search in a deep true triaxial stress state. Meanwhile, due to the deep high-disturbance stress environment, the research angle of rock mechanics has gradually shifted from macro-statics to mesoscopic rock dynamics, so the discipline of rock mechanics has also taken a brand-new road.

The research of rock mechanics relies on a high-performance rock mechanics test machine. At present, many true triaxial stress test machines for deep surrounding rocks have been able to apply a disturbance stress based on a static force to research the rock mechanical properties under a dynamic disturbance state. However, the existing disturbance rock mechanics test machine is limited by power consumption and performance, and only can continuously perform application for 5-10 minutes under high-frequency disturbance. However, in the deep engineering site, the disturbance stress of a tunnel face is present all the time with the tunneling process and is propagated further in the axial direction of the tunnel to act on a surrounding rock of a deep tunnel. The action time of the disturbance is much longer than the threshold (5-10 minutes) of the existing test machine. The time-dependent dynamic disturbance will lead to high-frequency fatigue opening and closing of cracks in the rock, affect the storage and release of internal energy of the hard rock, and change the characteristics of ductility and brittleness of the rock. Finally, brittle rupture with time effect occurs. The occurrence of time-delay rock burst is probably related to the disturbance influence with long time-dependent dynamic, high frequency and low amplitude.

To the above scientific problems, it is necessary to obtain the mechanical behavior of the deep hard rock under the action of the time-dependent dynamic disturbance stress. The present invention provides a true triaxial time-dependent dynamic disturbance test device for a deep-buried hard rock, which performs related test research on the mechanical behavior under the surrounding rock disturbance stress state in tunneling process of a large deep-buried hard rock, thereby providing effective help for the construction of major engineering infrastructure in China.

SUMMARY

In view of the shortcomings in the prior art, the present invention provides a true triaxial time-dependent dynamic disturbance test device for a deep-buried hard rock, including a test sample basic platform, wherein the test sample basic platform is provided with a hydrostatic pressure chamber, the hydrostatic pressure chamber forms a closed cavity structure by a pressure chamber top cover, a pressure chamber side wall and a pressure chamber bottom, and a flexible static load loading assembly, a test sample placing platform and an interlocking rigid clamp assembly are arranged in the hydrostatic pressure chamber.

A rigid loading system is arranged outside the test sample basic platform, and the rigid loading system includes two rigid static load loading assemblies and two rigid dynamic load loading assemblies, the rigid static load loading assemblies include a first rigid static load loading assembly and a second rigid static load loading assembly, and the rigid dynamic load loading assemblies include a first rigid dynamic load loading assembly and a second rigid dynamic load loading assembly; the first rigid static load loading assembly is arranged in a $\sigma_1$ principle stress loading direction and applies a $\sigma_1$-direction static load to a rock test sample, the pressure chamber side wall is provided with a first reacting force support in the $\sigma_1$ principle stress loading direction, and the first reacting force support provides a reacting force of the $\sigma_1$-direction static load; the second rigid static load loading assembly is arranged in a $\sigma_2$ principle stress loading direction and applies a $\sigma_2$-direction static load to the rock test sample, the pressure chamber top cover is provided with a second reacting force support in the $\sigma_2$ principle stress loading direction, and the second reacting force support provides a reacting force of the $\sigma_2$-direction static load; the first rigid dynamic load loading assembly is arranged on a side opposite to the second rigid static load loading assembly and applies the $\sigma_2$ principle stress loading direction disturbance stress to the rock test sample; and the second rigid dynamic load loading assembly is arranged on a side opposite to the first rigid static load loading assembly and applies a $\sigma_1$-direction disturbance stress to the rock test sample.

The interlocking rigid clamp assembly includes four test sample clamps, the test sample clamps (12) includes a first test sample clamp (12_a_), a second test sample clamp (12_b_), a third test sample clamp (12_c_) and a fourth test sample clamp (12_d_), the first test sample clamp and the third test sample clamp are arranged oppositely on two sides of the rock test sample in the $\sigma_1$ principle stress loading direction, the second test sample clamp and the fourth test sample clamp are arranged oppositely on two sides of the rock test sample in the $\sigma_2$ principle stress loading direction, and the four test sample clamps are mutually slidingly connected in an interlocking manner; the pressure chamber side wall is provided with a first loading piston at a position corresponding to the first test sample clamp, the first loading piston is embedded into the pressure chamber side wall and slidingly connected, and the first loading piston is in contact with the first test sample clamp; the pressure chamber bottom is provided with a second loading piston at a position corresponding to the fourth test sample clamp, the second loading piston is embedded into the pressure chamber bottom and slidingly connected, and the second loading piston is in contact with the fourth test sample clamp; the pressure chamber sidewall is fixedly provided with a first reacting force support at a position corresponding to the third test sample clamp, the first reacting force support is fixedly connected to the pressure chamber side wall, and the first reacting force support is in contact with the third test sample clamp; and the pressure chamber top cover is fixedly provided with a second reacting force support at a position corresponding to the second test sample clamp, the second reacting force support is fixedly connected to the pressure chamber top cover, and the second reacting force support is in contact with the second test sample clamp.

The rigid dynamic load loading assemblies further include dynamic actuators and dynamic self-balancing pistons, the third test sample clamp and the first reacting force support are provided with disturbance holes in the $\sigma_1$ principle stress loading direction, the second test sample clamp and the second reacting force support are provided with disturbance holes in the $\sigma_2$ principle stress loading direction, disturbance rods are arranged in the disturbance holes, the dynamic actuators, the dynamic self-balancing pistons and the disturbance rods are sequentially in contact with each other, and when the dynamic actuators work, the dynamic actuators apply $\sigma_1$-direction and $\sigma_2$-direction point disturbances to the rock test sample through the disturbance rods.

The rigid static load loading assembly include static actuators and static self-balancing pistons, the first rigid static load loading assembly is in contact with the first loading piston, and the $\sigma_1$-direction static load is applied to the rock test sample sequentially through the first loading piston and the first test sample clamp; and the second rigid static load loading assembly is in contact with the second loading piston, and the $\sigma_2$-direction static load is applied to the rock test sample sequentially through the second loading piston and the fourth test sample clamp.

The four test sample clamps are mutually slidingly connected in an interlocking manner, and mutual extrusion of the test sample clamps is capable of being avoided when rigid loading is applied.

The interlocking rigid clamp assembly is further provided with deformation sensors and deformation sensor supports, the deformation sensors include a first deformation sensor, a second deformation sensor, a third deformation sensor and a fourth deformation sensor, the deformation sensor supports include a first deformation sensor support, a second deformation sensor support, a third deformation sensor support and a fourth deformation sensor support the first deformation sensor is arranged in the first test sample clamp, the first deformation sensor support is arranged in the third test sample clamp, the second deformation sensor is arranged in the fourth test sample clamp, the second deformation sensor support is arranged in the second test sample clamp, the third deformation sensor and the third deformation sensor support are arranged in a $\sigma_3$ loading direction, and. Each of the first deformation sensors in $\sigma_1$ and $\sigma_2$ loading directions includes a contact needle, a disk spring telescopic rod and an LVDT sensor main body, and is a sliding orthogonal deformation LVDT sensor measurement structure; the third deformation sensor in the $\sigma_3$ loading direction includes a metal rod, a positioning block and an LVDT sensor, and is a fixed double-span beam LVDT sensor measurement structure; force-measuring sensors are respectively arranged in the first loading piston and the second loading piston, and are used to monitor real-time stress and strain in a static loading process in the $\sigma_1$ and $\sigma_2$ principle stress loading directions; and the interlocking rigid clamp assembly is further provided with an acoustic emission receiver and the acoustic emission receiver is capable of detecting sound emitted by the rock test sample during rupture.

Further, the device further includes a disturbance mode controller, the dynamic actuator is controlled by the disturbance mode controller, and the disturbance mode controller is capable of selecting the disturbance mode according to an oil temperature and a power consumption of a servo oil source device and is capable of applying a disturbance stress in a long time-dependent dynamic rheological test; the disturbance mode controller includes an intelligent oil source monitoring device and a rheological test recording device; the intelligent oil source monitoring device is arranged in the disturbance rod, used to detect the oil temperature of the servo oil source device and send oil temperature information to the disturbance mode controller, and used to perform scram braking on disturbance loading control of a warning temperature so as to deal with the situation that the temperature of the disturbance rod is too high and out of control under special circumstances and increase the success rate of the rheological test; and the rheological test process recording device is used to record a rheological test duration, a disturbance stress application duration, a power consumption of the test machine, a real-time stress-strain curve of the rock test sample and other information.

Further, the device further includes an intelligent information control and rupture sensing system having a closed-loop servo control working mode, and the intelligent information control and rupture sensing system comprises a $\sigma_1$ system, a $\sigma_2$ system, a $\sigma_3$ system and a time-dependent dynamic disturbance intelligent control center.

The $\sigma_1$ system is provided with a first disturbance mode controller, and monitors and controls the static actuators and the dynamic actuators in the $\sigma_1$ principle stress loading direction; the $\sigma_2$ system is provided with a second disturbance mode controller, and monitors and controls the static actuators and the dynamic actuators in the $\sigma_2$ principle stress loading direction; and the $\sigma_3$ system is provided with a third disturbance mode controller, and monitors and controls the flexible static load loading assembly in a $\sigma_3$ principle stress loading direction. The first disturbance mode controller, the second disturbance mode controller and the third disturbance mode controller are capable of monitoring the oil temperature and the power consumption of the servo oil source device and selecting a disturbance mode according to the oil temperature and the power consumption of the servo oil source device, is capable of applying a disturbance stress in a long time-dependent dynamic rheological test, and is also capable of performing scram braking on a disturbance loading control of a warning temperature.

The time-dependent dynamic disturbance intelligent control center includes a computer and rheological test operation software, is capable of intelligently monitoring stress strain and rupture information of the rock test sample in a whole time-dependent dynamic disturbance process, is capable of controlling a static stress loading and unloading level, a disturbance stress application condition and other functions in real time, and is also capable of displaying a disturbance duration, a rheological loading duration, a real-time power consumption and disturbance load maintenance intelligent switching information in a time-dependent dynamic disturbance process; and the stress strain and rupture information is monitored in real time respectively by a force-measuring sensor, a deformation sensor and an acoustic emission receiver arranged on each direction, and is fed back to the computer.

The computer includes a large-capacity storage function, a test process intelligent switching sampling spacing function, disturbance load maintenance intelligent switching, a data intelligent filtering function and a rheological test process recording function, wherein the large-capacity storage function provides a storage space for long time-dependent dynamic disturbance data; the test process intelligent switching sampling spacing function is capable of reducing the acquisition of useless data; the data intelligent filtering function is capable of filtering meaningless disturbance stress records in a disturbance rheological process; and the rheological test process recording function is used to record a rheological test duration, a disturbance stress application duration, a temperature, a power consumption and real-time stress-strain curve information of the rock test sample.

The rheological test operation software first loads the rock test sample to an initial-stage stress level, at this time, oil source power consumption monitoring and intelligent switching cooperate with each other to complete a first-stage disturbance load maintenance and static load maintenance process, and for an occurrence of test emergency braking caused by too high power consumption and too high oil temperature of the servo oil source device in the time-dependent dynamic disturbance process, disturbance is intelligently stopped when the disturbance stress is applied close to a power consumption limit, including the following steps:

step 1: presetting a total loading-stage rheological duration;

step 2: performing disturbance load maintenance, determining to switch to static load maintenance according to the monitored oil source temperature of the servo oil source device, feeding information back to the dynamic actuators by the oil source power consumption monitoring after the oil temperature of the servo oil source device is reduced, continuously performing disturbance load maintenance, and repeating the process;

step 3: determining a state of the rock test sample through stress strain and rupture information, stopping loading immediately if damage occurs, and ending the test;

step 4: if the rock test sample in step 3 is not damaged, continuously increasing a stress in a maximum main stress direction to a second stage; and step 5: repeating step 1 to step 4 until the rock test sample is damaged, stopping loading immediately, and ending the test.

Further, the device further includes a rigid loading system framework, wherein the first rigid static load loading assembly and the second rigid dynamic load loading assembly are connected to the test sample basic platform through the rigid loading system framework, the rigid loading system framework is sleeved outside the test sample basic platform and is slidingly connected to the test sample basic platform, and a hydraulic lifting mechanism is arranged at a lower end of the test sample basic platform; the hydrostatic pressure chamber is of semi-closed cavity structure, and the hydrostatic pressure chamber is in an open state after the test sample basic platform descends; and after the test sample basic platform ascends, the rigid loading system framework closes the hydrostatic pressure chamber, the second rigid dynamic load loading assembly is in contact with the disturbance rods, and the first static load loading assembly is in contact with the first loading piston.

The static actuators and the dynamic actuators are connected to travel-measuring sensors, and the travel-measuring sensors are used to monitor a displacement of the static actuators and the dynamic actuators when load is applied.

The technical solutions provided by the present invention at least have the following beneficial effects:

(1) The rigid static load loading assembly and the rigid dynamic load loading assembly are used to apply wide-amplitude-frequency dynamic disturbance stresses in different true triaxial main stress directions to simulate the true disturbance stress state of the deep engineering rock, thereby achieving long time-dependent static and disturbance stress coupled application control of the rock in the true triaxial disturbance stress state, and being suitable for deep mine rock masses and deep-buried tunnel engineering surrounding rocks as test objects of the test. The peak property, the brittle failure mode, the energy storage condition, the deformation property and other physical and mechanical behaviors of the rock under the true triaxial disturbance stress state are researched according to the field detection of different power disturbance frequencies and amplitudes. A dynamic test can be performed on surrounding rocks with different properties, such as a jointed rock mass, a brittle rock mass and an altered rock mass, the three-dimensional stress state can be adjusted freely in the rheological process, the compression deformation, the rupture information and the time-dependent dynamic disturbance mechanical behavior of the rocks can be observed in real time, and a hard rock true triaxial dynamic constitutive model with effect under the action of the true triaxial disturbance stress can be established.

(2) A three-dimensional stress loading system with combined loading of the flexible static load loading assembly, the rigid dynamic load loading assembly and the rigid static load loading assembly is used, and rigid dynamic load is provided with a disturbance rod in a loading direction, so that coaxial disturbance loading and unloading under different initial static stresses and in different main stress directions are achieved. A "point" disturbance mode is converted into a "face" disturbance mode through the disturbance rod, a disturbance hole and a test sample clamp, so that a disturbance mode more suitable for an actual working condition on site is provided while power consumption is reduced and time-dependent dynamic disturbance is achieved.

(3) A closed-loop servo control system is used to dynamically control the disturbance process and reasonably control and distribute the power consumption of the test machine to achieve the rheological dynamic test of loading and unloading disturbance, is suitable for the deep engineering surrounding rock subjected to the disturbance stress for a long time, and can simulate the time-dependent related rock dynamic rheological mechanisms research under the conditions of different surrounding rock stresses, and high and low frequencies and high and low amplitudes of different dynamic disturbances.

(4) The loading mode of "two rigidities and one flexibility" is used to reduce the influence of stress blank angle shear under the action of the time-dependent disturbance true triaxial stress and can be suitable for small-size test samples. The small-size test samples are conveniently applied to the ultra-deep drilling and coring rock test sample test, and can reduce the influence of random results caused by the homogeneity of the rocks. There are various kinds of test samples. The true triaxial time-dependent dynamic disturbance physical and mechanical test can be performed on deep hard rocks, soft rocks, altered rocks, jointed rocks and rock-like test samples.

REFERENCE NUMERALS OF THE DRAWINGS

- 1: test sample basic platform; 11: hydrostatic pressure chamber; 12: test sample clamp; 12*a*: first sample clamp; 12*b*: second sample clamp; 12*c*: third sample clamp; 12*d*: fourth sample clamp; 13: rock test sample; 14: loading piston; 14*a*: first loading piston; 14*b*: second loading piston; 15: reacting force support; 15*a*: first reacting force support; 15*b*: second reacting force support;
- 2: rigid static load loading assembly; 2*a*: first rigid static load loading assembly; 2*b*: second rigid static load loading assembly; 21: static actuator; 22: static self-balancing piston;
- 3: rigid dynamic load loading assembly; 3*a*: first rigid dynamic load loading assembly; 3*b*: second rigid dynamic load loading assembly; 31: dynamic actuator; 32: dynamic self-balancing piston; 33: disturbance rod;
- 4: rigid loading system framework;
- 5: force-measuring sensor;
- 6: deformation sensor; 6*a*: first deformation sensor; 6*b*: second deformation sensor; 6*c*: third deformation sensor; 61: deformation sensor support; 61*a*: first deformation sensor support; 61*b*: second deformation sensor support; 61*c*: third deformation sensor support;
- 7: acoustic emission receiver;
- 8: travel-measuring sensor;
- X: $\sigma_1$ principle stress loading direction; Y: $\sigma_2$ principle stress loading direction; Z: $\sigma_3$ principle stress loading direction.

DETAILED DESCRIPTION OF THE EMBODIMENTS

The present invention will be further described below in detail with reference to the accompanying drawings and the specific embodiments.

Embodiment 1

Figure 1:
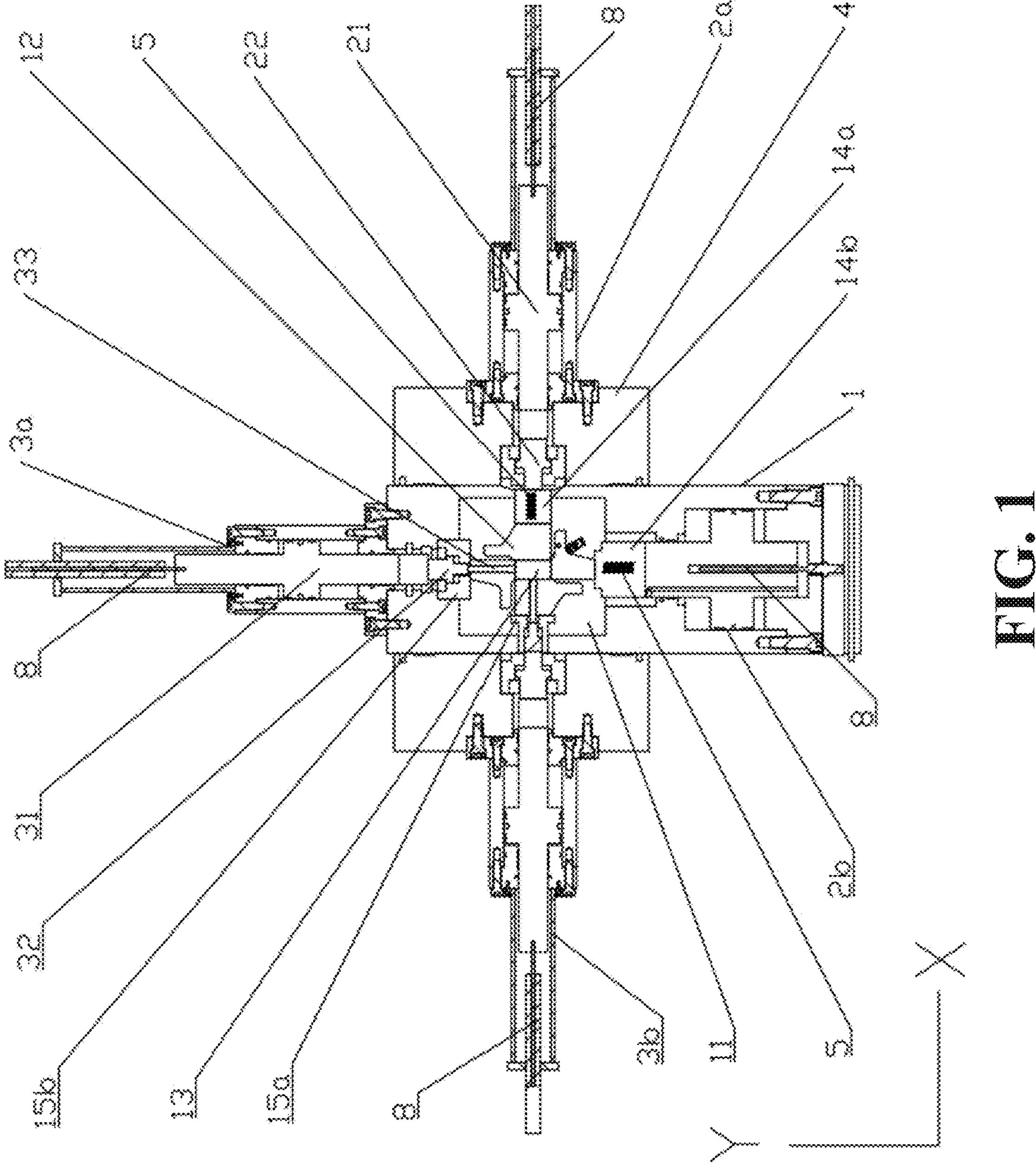
FIG. 1 is a schematic structure of a sectional structure of a true triaxial time-dependent dynamic disturbance test device for a deep-buried hard rock.
Figure 2:
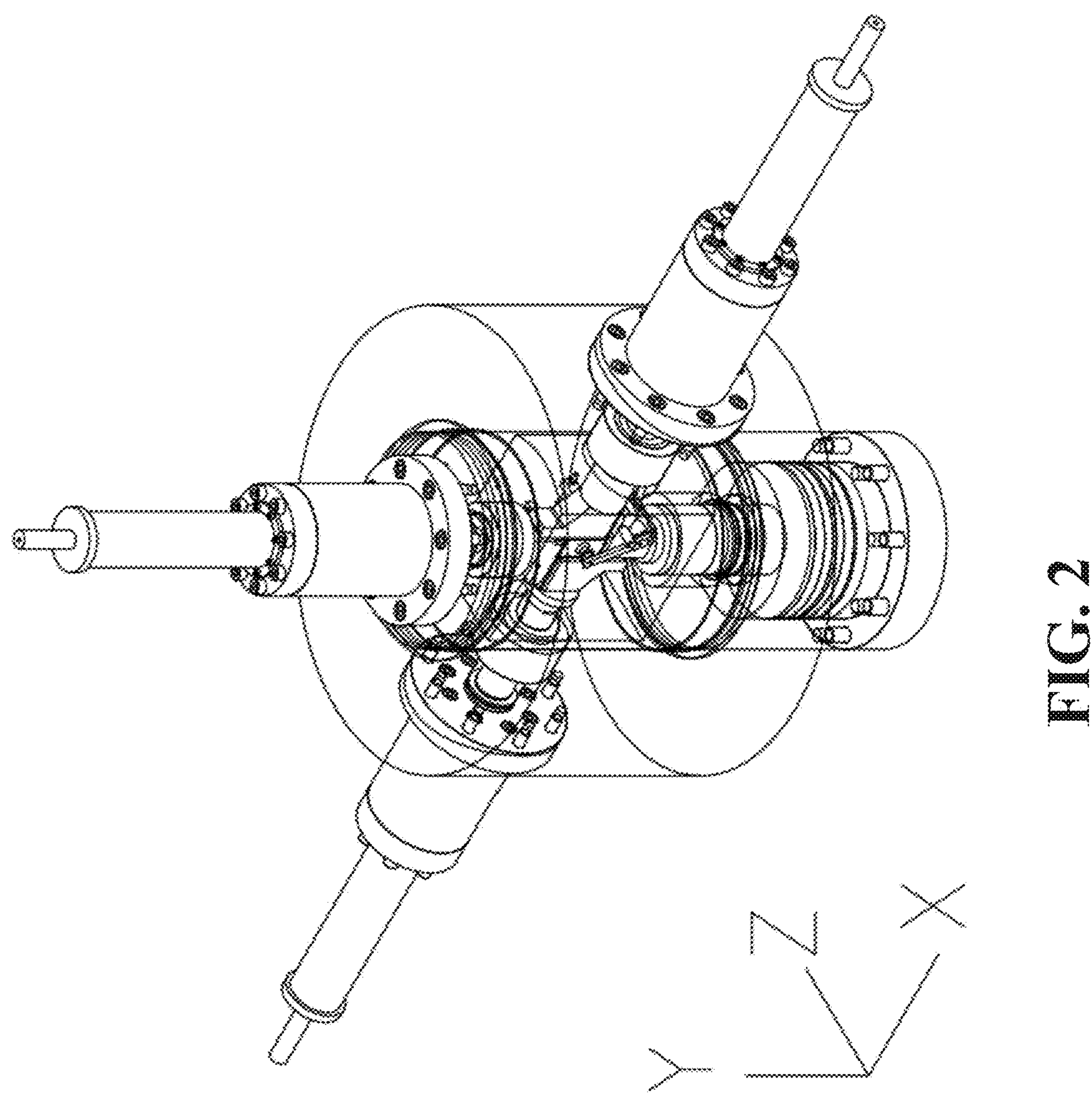
FIG. 2 is a schematic structure of a three-dimensional structure of a true triaxial time-dependent dynamic disturbance test device for a deep-buried hard rock.
Figure 5:
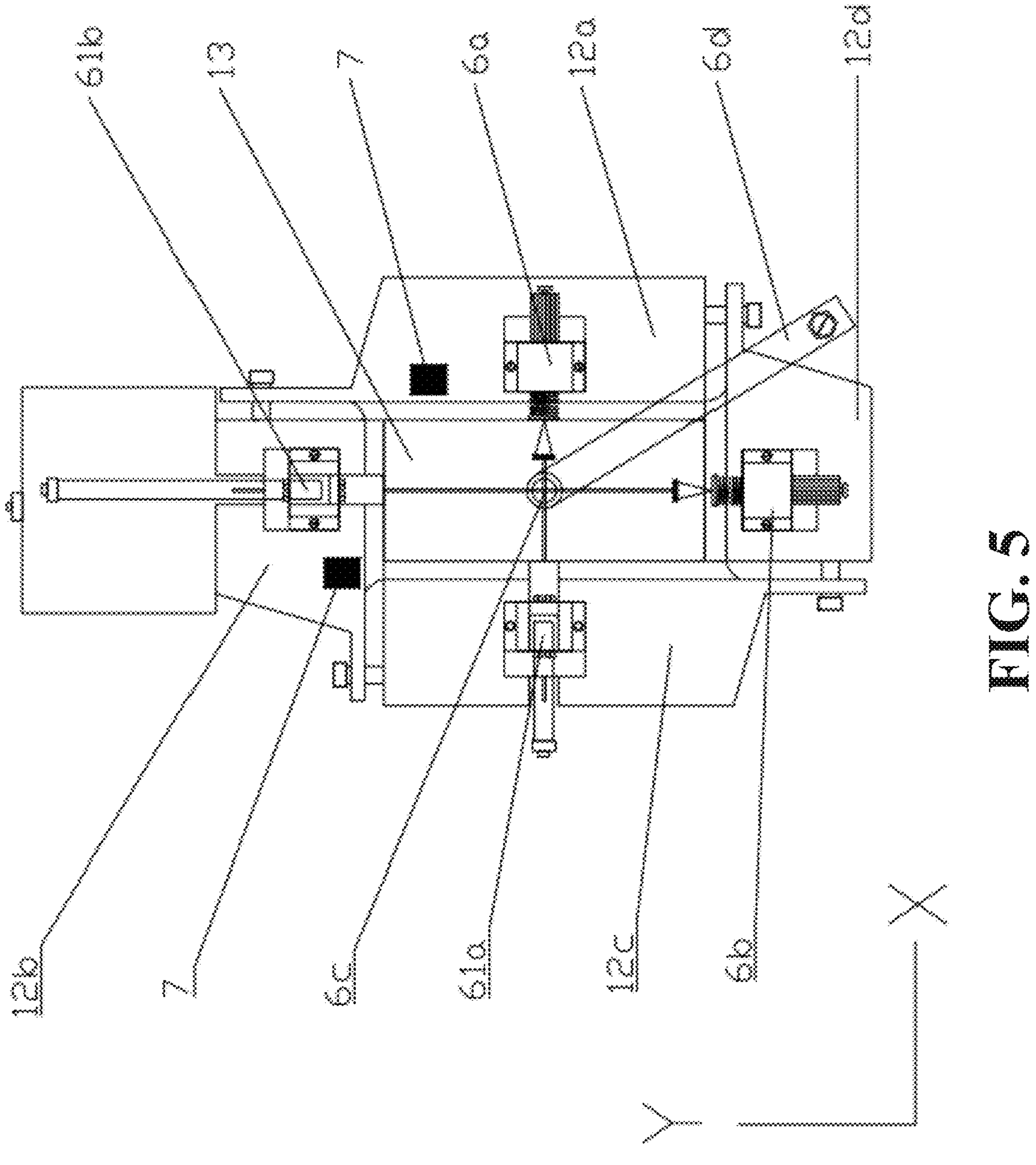
FIG. 5 is a structural schematic diagram of an interlocking rigid clamp assembly.

Referring to FIG. 1, FIG. 2 and FIG. 5, a true triaxial time-dependent dynamic disturbance test device for a deep-buried hard rock includes a test sample basic platform 1. The test sample basic platform 1 is provided with a hydrostatic pressure chamber 11, the hydrostatic pressure chamber 11 forms a closed cavity structure by a pressure chamber top cover, a pressure chamber side wall and a pressure chamber bottom, and the pressure chamber top cover is manufactured by high-strength alloy through one-molding process and is equipped with a high-pressure seal ring. A test sample placing platform and an interlocking rigid clamp assembly are arranged in the hydrostatic pressure chamber 11, and the test sample placing platform is constructed by large-area hollow metal and reserved with a test sample fixing hole. The interlocking rigid clamp assembly includes four test sample clamps 12, the test sample clamps 12 comprises a first test sample clamp 12*a*, a second test sample clamp 12*b*, a third test sample clamp 12*c* and a fourth test sample clamp 12*d*, the first test sample clamp 12*a* and the third test sample clamp 12*c* are arranged oppositely on two sides of the rock test sample 13 in a $\sigma_1$ principle stress loading direction, the second test sample clamp 12*b* and the fourth test sample clamp 12*d* are arranged oppositely on two sides of the rock test sample 13 in a $\sigma_2$ principle stress loading direction, and the four test sample clamps 12 are mutually sliding connected in an interlocking manners, so that mutual extrusion of the test sample clamps 12 can be avoided when rigid loading is applied. The pressure chamber side wall is provided with a first loading piston 14*a* at a position corresponding to the first test sample clamp 12*a*, the first loading piston 14*a* is embedded into the pressure chamber side wall and slidingly connected, and the first loading piston 14*a* is in contact with the first test sample clamp 12*a* and can transfer an external stress to the rock test sample 13. The pressure chamber bottom is provided with a second loading piston 14*b* at a position corresponding to the fourth test sample clamp 12*d*, the second loading piston 14*b* is embedded into the pressure chamber bottom and slidingly connected, and the second loading piston 14*b* is in contact with the fourth test sample clamp 12*d* and can transfer an external stress to the rock test sample 13. The pressure chamber side wall is fixedly provided with a first reacting force support 15*a* at a position corresponding to the third test sample clamp 12*c*, the first reacting force support 15*a* is fixedly connected to the pressure chamber side wall, and the first reacting force support 15*a* is in contact with the third test sample clamp 12*c* and can provide a reacting force of a static load in the $\sigma_1$ principle stress loading direction. The pressure chamber top cover is fixedly provided with a second reacting force support 15*b* at a position corresponding to the second test sample clamp 12*b*, the second reacting force support 15*b* is fixedly connected to the pressure chamber top cover, and the second reacting force support 15*b* is in contact with the second test sample clamp 12*b* and can provide a reacting force of a static load in the $\sigma_2$ principle stress loading direction.

A rigid loading system is arranged outside the test sample basic platform 1, and the rigid loading system includes two rigid static load loading assemblies 2 and two rigid dynamic load loading assemblies 3, the rigid static load loading assemblies (2) comprise a first rigid static load loading assembly (2*a*) and a second rigid static load loading assembly (2*b*), and the rigid dynamic load loading assemblies (3) comprise a first rigid dynamic load loading assembly (3*a*) and a second rigid dynamic load loading assembly (3*b*). The rigid static load loading assemblies 2 include static actuators 21 and static self-balancing pistons 22. The static actuators 21 are a structure in the prior art, are powered by a servo oil source device and can apply a static load. The first rigid static load loading assembly 2*a* is arranged in the $\sigma_1$ principle stress loading direction and is in contact with the first loading piston 14*a*. During work, the static load of the first rigid static load loading assembly 2*a* is applied to the rock test sample 13 sequentially through the first loading piston 14*a* and the first test sample clamp 12*a*, a $\sigma_1$-direction static load is applied to the rock test sample 13, the first reacting force support 15*a* provides a reacting force of the $\sigma_1$-direction static load, and the maximum load of the first rigid static load loading assembly 2*a* is 400 kN (640 MPa).

The second rigid static load loading assembly 2*b* is arranged in the $\sigma_2$ principle stress loading direction and is in contact with the second loading piston 14*b*. During work, the static load of the second rigid static load loading assembly 2*b* is applied to the rock test sample 13 sequentially through the second loading piston 14*b* and the fourth test sample clamp 12*d*, a $\sigma_2$-direction static load is applied to the rock test sample 13, the second reacting force support 15*b* provides a reacting force of the $\sigma_2$-direction static load, and the maximum load of the second rigid static load loading assembly 2*b* is 50 kN (40 MPa).

The rigid dynamic load loading assemblies 3 include dynamic actuators 31 and dynamic self-balancing pistons 32. The dynamic actuators 31 are a structure in the prior art, are powered by a servo oil source device and can apply a disturbance stress. The third test sample clamp 12*c* and the first reacting force support 15*a* are provided with disturbance holes in the $\sigma_1$ principle stress loading direction. The second test sample clamp 12*b* and the second reacting force support 15*b* are provided with disturbance holes in the $\sigma_2$ principle stress loading direction. The disturbance holes serve as disturbance stress applying channels. Disturbance rods 33 are arranged in the disturbance holes. The dynamic actuators 31, the dynamic self-balancing pistons 32 and the disturbance rods 33 are sequentially in contact with each other. When the dynamic actuators 31 work, the dynamic actuators 31 apply $\sigma_1$-direction and $\sigma_2$-direction point disturbances to the test sample clamp 12 through the disturbance rods 33, with the maximum amplitude of 10 MPa and the maximum disturbance frequency of 80 Hz. The test sample clamp 12 transfers the disturbance to the rock test sample 13. The disturbance mode is changed from a point disturbance to a surface disturbance. Due to the stable static loading and stable positions of the disturbance holes, the dynamic disturbance loading also can be applied stably in the rheological process.

A flexible static load loading assembly is further arranged in the hydrostatic pressure chamber 11. In this embodiment, the flexible static load loading assembly is a confining pressure loading mode in the prior art, includes a needle valve, a high-pressure oil pipe and a hydraulic piston, and is powered by the servo oil source device. During work, the flexible static load loading assembly can apply a confining type static load to the rock test sample 13, with the maximum confining pressure of 40 MPa.

When the device works, the static load loading mode of “two rigidities and one flexibility” on the rock test sample 13 is achieved through the rigid static load loading assemblies 2 and the flexible static load loading assembly, thereby ensuring the application of a true triaxial stress and no stress blank angle. The “two rigidities” is rigid loading in the $\sigma_1$ and $\sigma_2$ principle stress loading directions and is applied by the rigid static load loading assemblies 2. The “one flexibility” is flexible loading in the $\sigma_3$ principle stress loading direction and is applied by the flexible static load loading assembly. The $\sigma_1$-direction and $\sigma_2$-direction disturbance stresses are applied by the dynamic load loading assemblies 3 to achieve the coupled application of the long time-dependent static and disturbance stress of the rock under the state of the true triaxial disturbance stress, and is particularly suitable for the deep engineering surrounding rock subjected to the disturbance stress for a long time. The time-dependent related rock dynamic rheological mechanisms research under the conditions of different surrounding rock stresses, and high and low frequencies and high and low amplitudes of different dynamic disturbances can be simulated.

Force-measuring sensors 5 are respectively arranged in the first loading piston 14*a* and the second loading piston 14*b*, and are used to monitor real-time stress and strain in a static loading process in the $\sigma_1$ and $\sigma_2$ principle stress loading directions. The real-time oil intake is determined through a servo valve, the power consumption is saved, and the stable control of the stress and strain of the test machine is ensured.

Referring to FIG. 5, the interlocking rigid clamp assembly is further provided with deformation sensors 6 and deformation sensor supports 61, the deformation sensors (6) comprise a first deformation sensor (6*a*), a second deformation sensor (6*b*) and a third deformation sensor (6*c*), the deformation sensor supports (61) comprise a first deformation sensor support (61*a*), a second deformation sensor support (61*b*) and a third deformation sensor support (61*c*), the first deformation sensor 6*a* is arranged in the first test sample clamp 12*a*, the first deformation sensor support 61*a* is arranged in the third test sample clamp 12*c*, the second deformation sensor 6*b* is arranged in the fourth test sample clamp 12*d*, the second deformation sensor support 61*b* is arranged in the second test sample clamp 12*b*, and the third deformation sensor 6*c* and the third deformation sensor support 61*c* are arranged in a $\sigma_3$ loading direction. Each of the deformation sensors 6 is a structure in the prior art, includes a disk spring telescopic rod and an LVDT sensor main body, is measured by a contact needle on the opposite site through contact, and is a sliding orthogonal deformation LVDT sensor measurement structure in the $\sigma_1$ and $\sigma_2$ principle stress loading directions. When the rock test sample 13 is deformed, the contact needle drives the telescopic rod of the LVDT sensor to move forward and backward to implement deformation measurement in the $\sigma_1$ and $\sigma_2$ principle stress loading directions. The third deformation sensor 6*c* is a fixed double-span beam LVDT sensor measurement structure in the $\sigma_3$ loading direction. the third deformation sensor 6*c* includes a metal rod, a positioning block and an LVDT sensor. When deformation occurs in the $\sigma_3$ principle stress loading direction, the position of the positioning block on the rock test sample 13 changes, and the telescopic rod of the LVDT sensor moves accordingly to implement deformation measurement in the $\sigma_3$ principle stress loading direction.

The interlocking rigid clamp assembly is further provided with an acoustic emission receiver 7, acoustic emission receiver 7 is capable of detecting sound emitted by the rock test sample 13 during rupture, monitors the rock test sample 13 in real time in a rheological test process and feeds information back to a computer.

Figure 6:
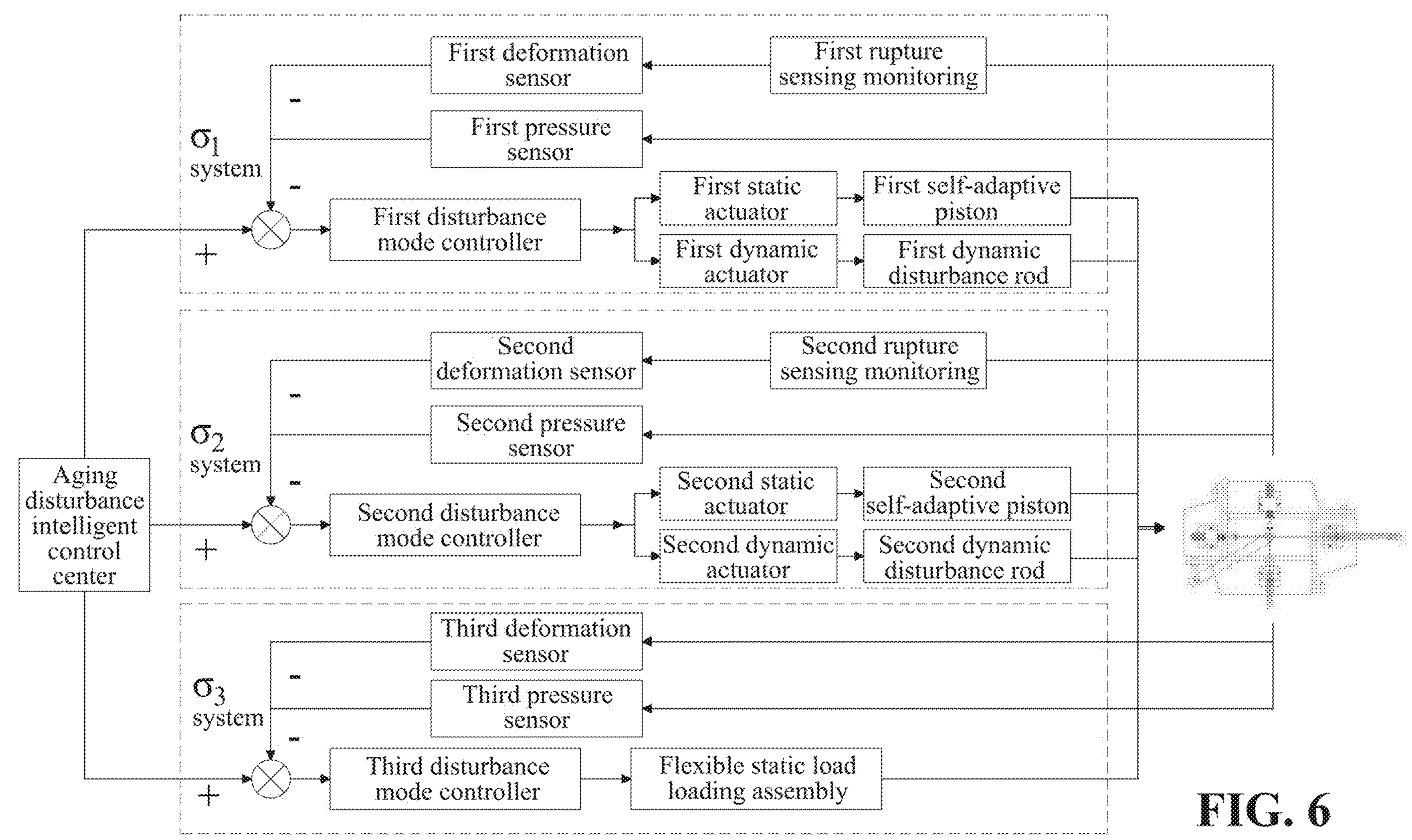
FIG. 6 is a schematic diagram of a closed-loop servo control working mode of an intelligent information control and rupture sensing system.

Referring to FIG. 6, the device further includes an intelligent information control and rupture sensing system having a closed-loop servo control working mode, and the intelligent information control and rupture sensing system includes a $\sigma_1$ system, a $\sigma_2$ system, a $\sigma_3$ system and a time-dependent dynamic disturbance intelligent control center.

The $\sigma_1$ system is provided with a first disturbance mode controller, and monitors and controls the static actuators 21 and the dynamic actuators 31 in the $\sigma_1$ principle stress loading direction; the $\sigma_2$ system is provided with a second disturbance mode controller, and monitors and controls the static actuators (21) and the dynamic actuators (31) in the $\sigma_2$ principle stress loading direction; and the $\sigma_3$ system is provided with a third disturbance mode controller, and monitors and controls the flexible static load loading assembly in a $\sigma_3$ principle stress loading direction. The first disturbance mode controller, the second disturbance mode controller and the third disturbance mode controller are the prior art, can monitor the oil temperature and the power consumption of the servo oil source device and select the disturbance mode according to the oil temperature and the power consumption of the servo oil source device, can apply a disturbance stress in a long time-dependent rheological test, and also can perform scram braking on a disturbance loading control of a warning temperature so as to deal with the situation that the temperature is too high and out of control under special circumstances and increase the success rate of the rheological test.

Figure 7:
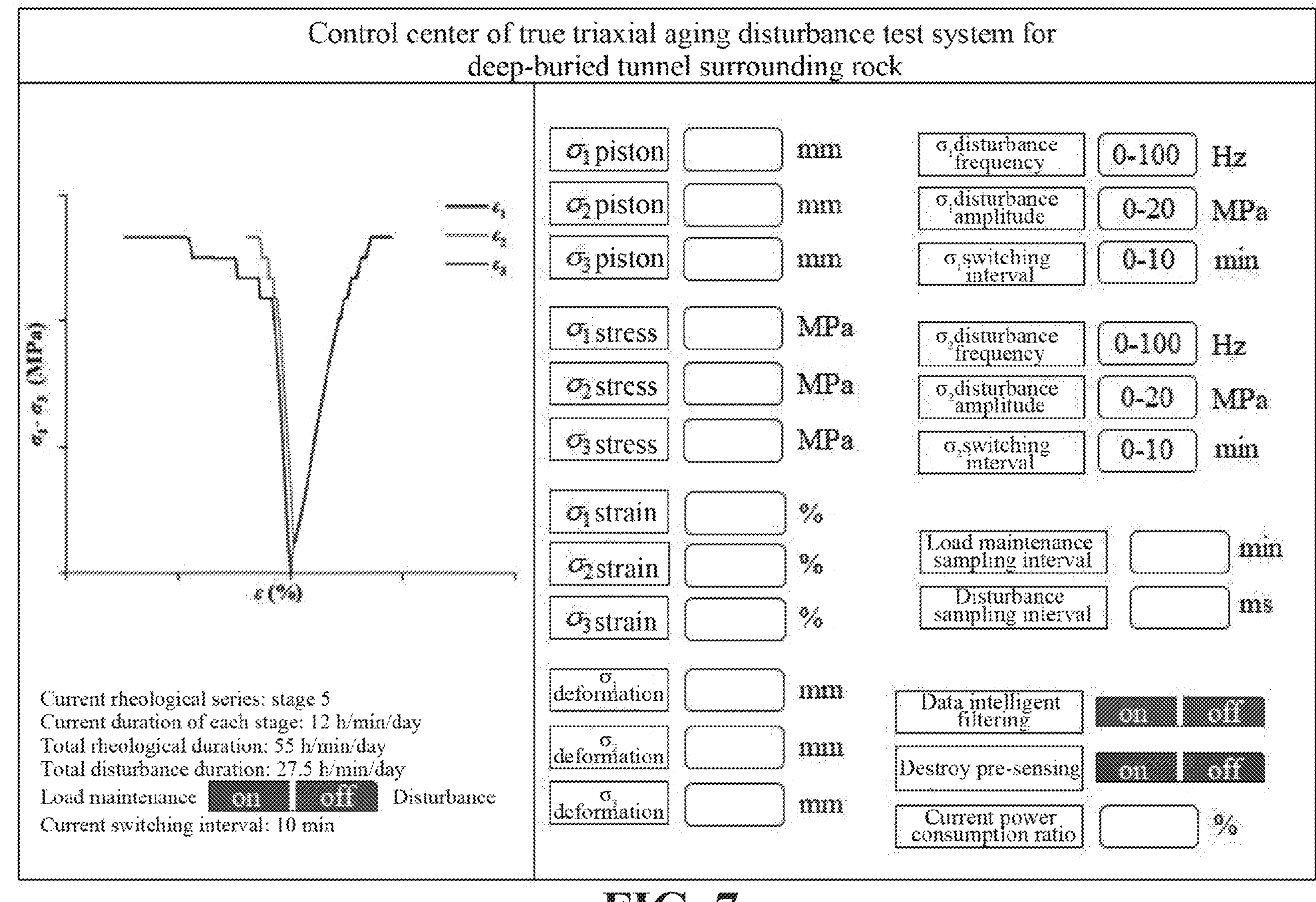
FIG. 7 is a schematic diagram of time-dependent dynamic disturbance intelligent control center.

Referring to FIG. 7, the time-dependent dynamic disturbance intelligent control center includes a computer and rheological test operation software, can intelligently monitor stress strain and rupture information of the rock test sample 13 in a whole time-dependent dynamic disturbance process, can control a static stress loading and unloading level, a disturbance stress application condition and other functions in real time, and also can display information in real time in the time-dependent dynamic disturbance process, such as a disturbance duration, a rheological loading duration, a real-time power consumption and a disturbance load maintenance intelligent switching function. Important information in the process of the true triaxial time-dependent disturbance dynamic test is monitored globally to ensure the smooth progress of the test. The stress strain and rupture information are monitored in real time respectively by the force-measuring sensor 5, the displacement sensor 6 and the acoustic emission receiver 7 arranged on each direction, and is fed back to the computer for real-time monitoring in the rheological test process.

The computer includes a large-capacity storage function, a test process intelligent switching sampling spacing function, disturbance load maintenance intelligent switching, a data intelligent filtering function and a rheological test process recording function; wherein the large-capacity storage function provides a storage space for long time-dependent dynamic disturbance data and retains data integrity; the test process intelligent switching sampling spacing function can reduce the acquisition of useless data as much as possible on the premise that the acquisition density allows, ensures the data integrity and is more conveniently applied to the rheological test; the data intelligent filtering function can filter meaningless disturbance stress records in a disturbance rheological process, reduce the quantity of test data and ensure the smooth progress of a long time-dependent rheological test sample; and the rheological test process recording function is used to record a rheological test duration, a disturbance stress application duration, a temperature, a power consumption, a real-time stress-strain curve of the rock test sample and other information.

Figure 8:
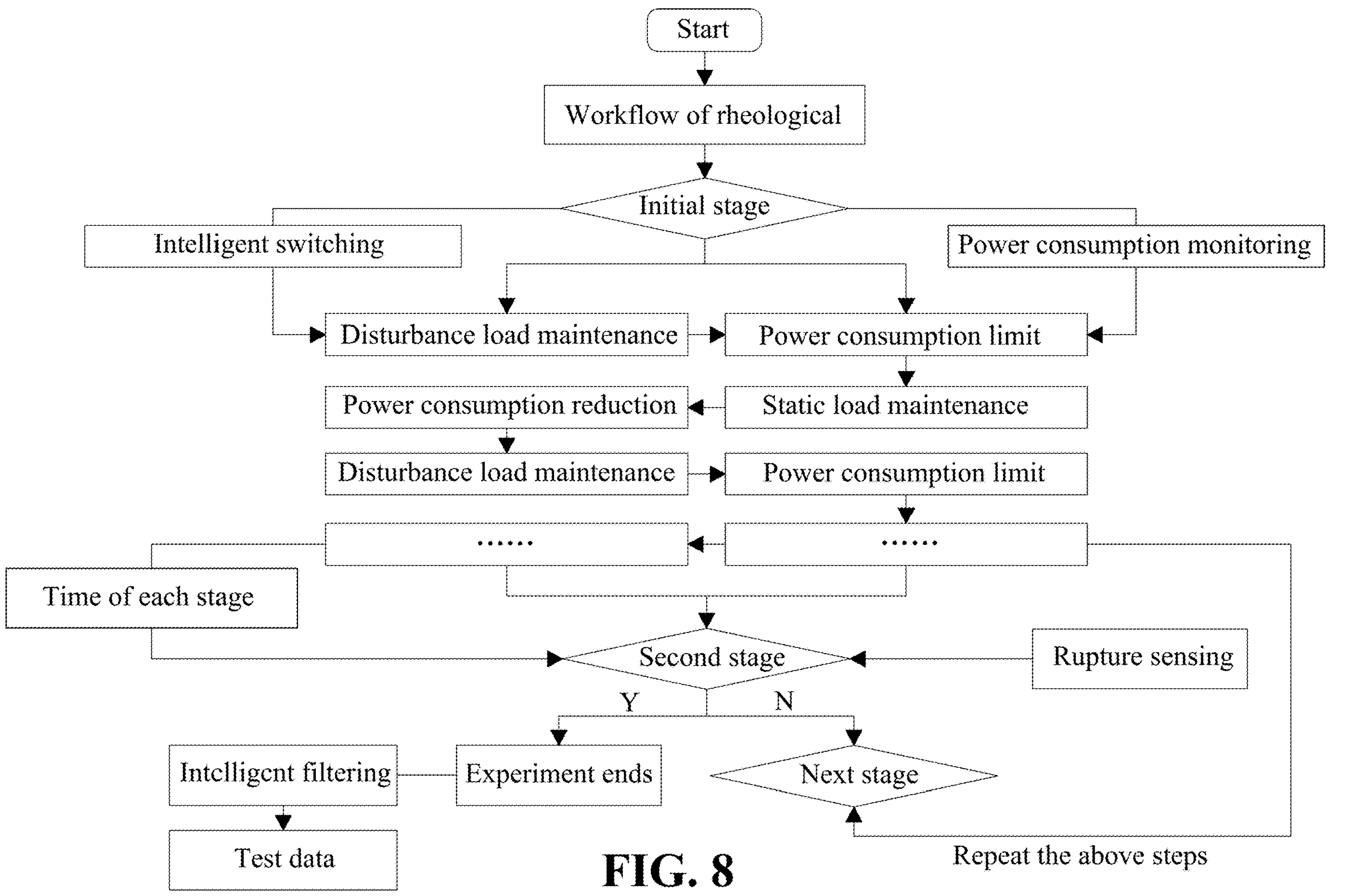
FIG. 8 is a flowchart of rheological test operation software.

Referring to FIG. 8, the rheological test operation software optimizes and improves the existing true triaxial test operation for the long time-dependent rheological test. The rock test sample (13) is first loaded to an initial-stage stress level, at this time, oil source power consumption monitoring and intelligent switching cooperate with each other to complete a first-stage disturbance load maintenance and static load maintenance process, and for an occurrence of test emergency braking caused by too high power consumption and too high oil temperature of the servo oil source device in the time-dependent dynamic disturbance process, the disturbance function is intelligently stopped when the disturbance stress is applied close to a power consumption limit, so as to ensure that the disturbance rheological test can break through the limit of the power consumption. The specific implementation method is as follows: a total loading-stage rheological duration is preset, and the loading-stage rheological test is started. Disturbance load maintenance is performed first, the oil temperature of the servo oil source device is monitored with power consumption to switch to static load maintenance, information is fed back to the dynamic actuators 31 by the oil source power consumption monitoring after the oil temperature of the servo oil source device is reduced, disturbance load maintenance is continuously performed, and the process is repeated. A state of the rock test sample 13 is determined through stress strain and rupture information in this process, loading is stopped immediately if damage occurs, and the test ends. If the rock test sample 13 is not damaged in this process, that is, after a preset rheological duration is reached, the rock test sample 13 still can bear the stress level of this stage, that is, after the stress in the maximum main stress direction is continuously increased to a second stage, a first-stage disturbance and static load maintenance process and loading to the next-stage process are repeated until the rock test sample 13 is damaged, that is, when stress data changes greatly and the ringing number of the acoustic emission receiver 7 is rapidly increased exponentially, loading is stopped immediately, thereby avoiding damage to the equipment and the state of the ruptured rock test sample 13.

Embodiment 2

Figure 3:
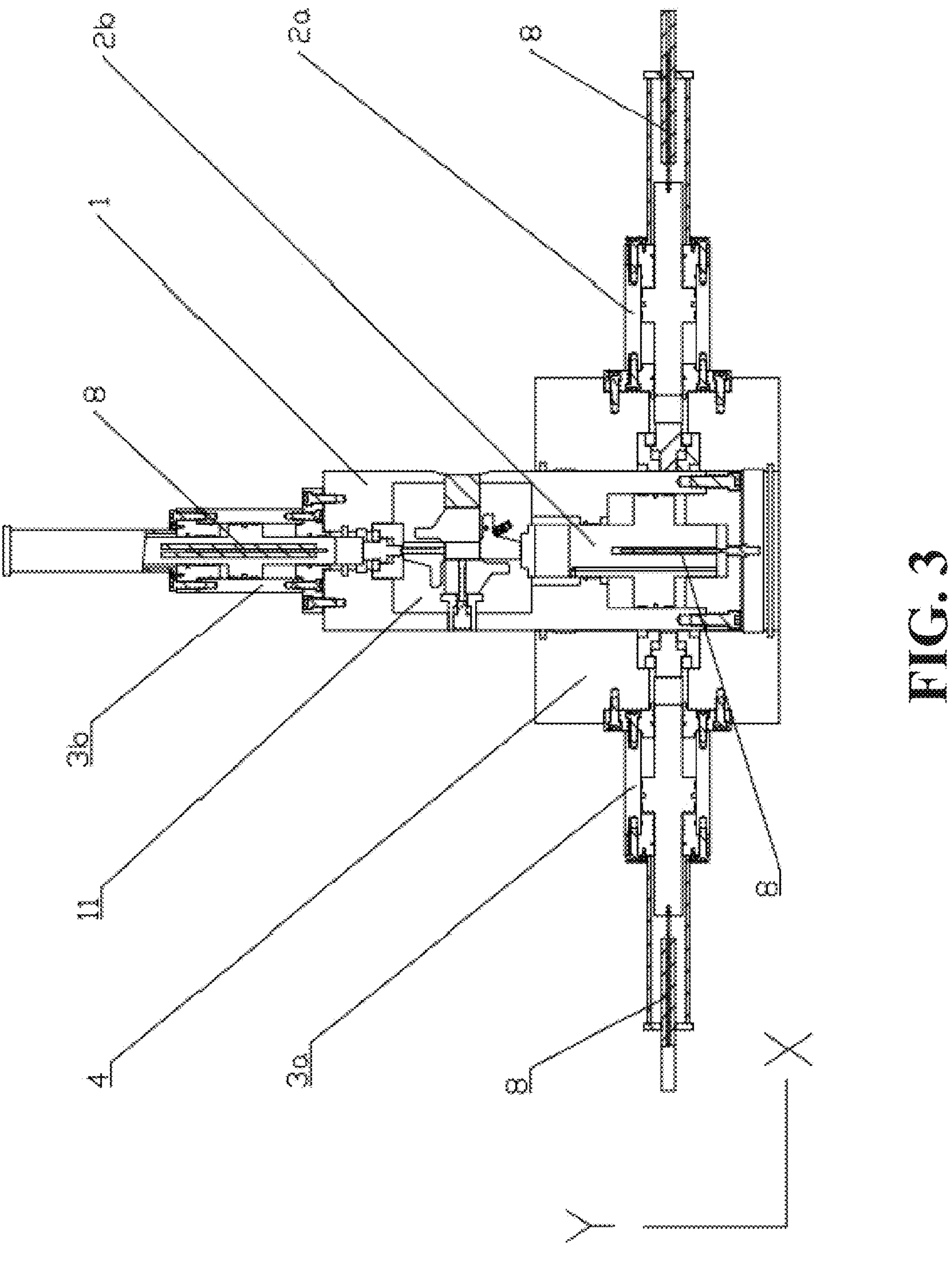
FIG. 3 is a schematic structure of a sectional structure of a descending state of a test sample basic platform.
Figure 4:
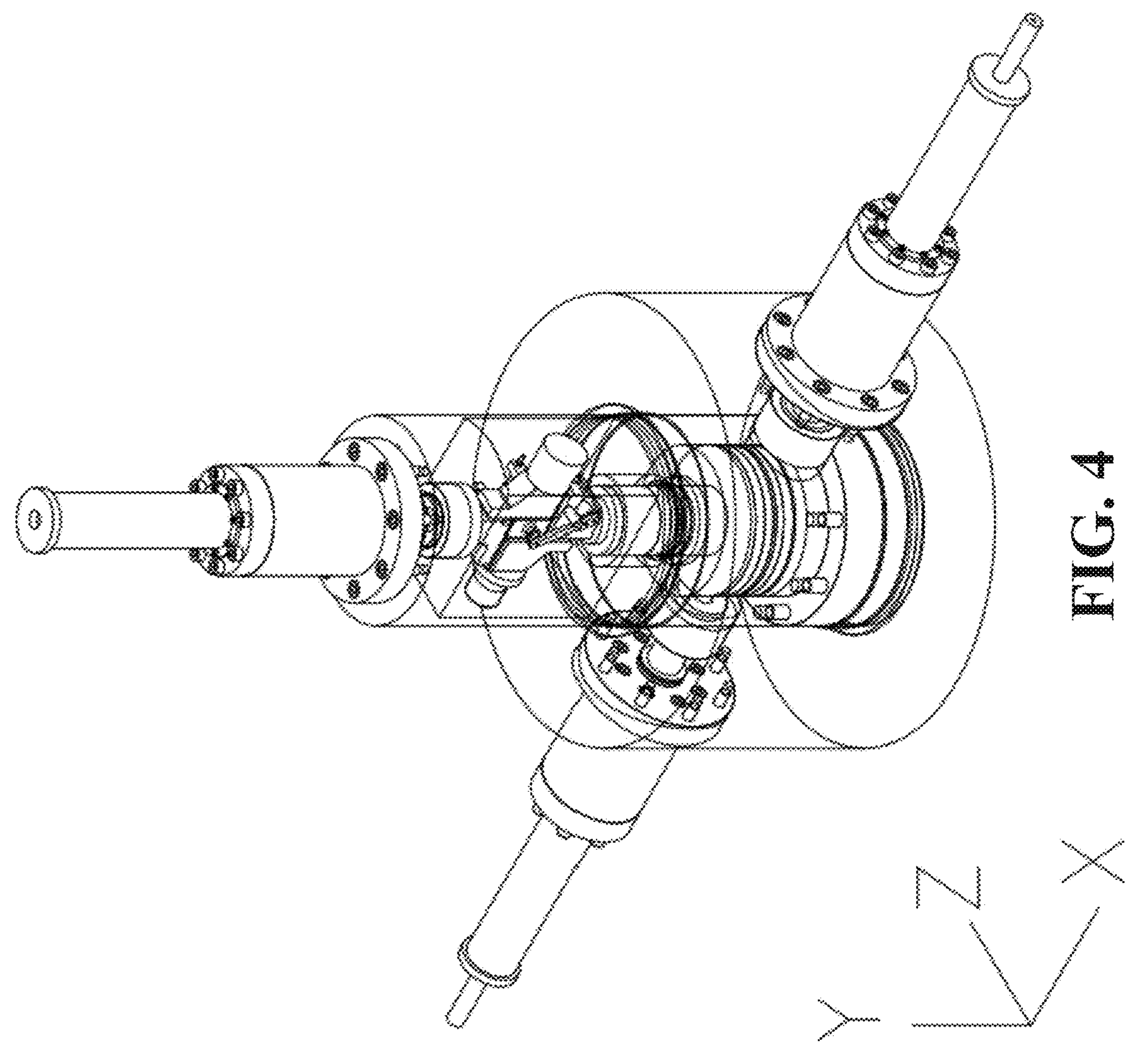
FIG. 4 is a schematic structure of a three-dimensional structure of a descending state of a test sample basic platform.

Referring to FIG. 3 and FIG. 4, other settings in this embodiment are the same as those in Embodiment 1, except that the device further includes a rigid loading system framework 4, the first rigid static load loading assembly 2*a* and the second rigid dynamic load loading assembly 3*b* are connected to the test sample basic platform 1 through the rigid loading system framework 4, the rigid loading system framework 4 is sleeved outside the test sample basic platform 1 and is slidingly connected to the test sample basic platform 1, a hydraulic lifting mechanism is arranged at a lower end of the test sample basic platform 1, the hydraulic lifting mechanism is a structure in the prior art, and during work, the hydraulic lifting mechanism can drive the test sample basic platform 1 to ascend and descend in the rigid loading system framework 4; the hydrostatic pressure chamber 11 is of semi-closed cavity structure, and after the test sample basic platform 1 descends, the hydrostatic pressure chamber 11 is in an open state, thereby facilitating the mounting operation of the rock test sample 13 and the interlocking rigid clamp assembly; after the test sample basic platform 1 ascends, the rigid loading system framework 4 closes the hydrostatic pressure chamber 11, so that the flexible static load loading assembly can apply a $\sigma_3$-direction static load to the rock test sample 13; and after the test sample basic platform 1 ascends, the second rigid dynamic load loading assembly 3*b* is in contact with the disturbance rods 33, and the first static load loading assembly 2*a* is in contact with the first loading piston 14*a*, so that a $\sigma_1$-direction static load and a disturbance stress are applied to the rock test sample 13.

Embodiment 3

Other settings in this embodiment are the same as those in Embodiment 1, except that the static actuators 21 and the dynamic actuators 31 are all connected to travel-measuring sensors 8 which are used to monitor a displacement of the static actuators 21 and the dynamic actuators 31 when a load is applied so as to prevent the applied load from exceeding the limit.

The use method and principle of the device are as follows: the rock test sample 13 is manufactured by a deep-buried site surrounding rock. Since the device is a static load loading mode of "two rigidities and one flexibility" and can ensure the application of the true triaxial stress and no stress blank angle, so the small-size rock test sample 13 can be selected, and the size of the rock test sample 13 selected in this embodiment is 25 mm×25 mm×50 mm. The test sample basic platform 1 is descended and the interlocking rigid clamp assembly is mounted. After mounting, gluing is performed in the $\sigma_3$ principle stress loading direction to prevent oil. After glue is dried, a clamp screw is removed and a displacement sensor 6 is mounted sequentially to measure the deformation of the test sample in real time in the true triaxial dynamic disturbance process. The mounted clamp is put on a test sample placing platform, a sensor line is connected to the controller, and the test sample placing platform is ascended to complete the preparation of the true triaxial dynamic disturbance test. The computer is turned on, confining pressures in three main stress directions are applied in the hydrostatic pressure chamber 11, a static prestress of 2 MPa to 3 MPa is applied through the static actuators 21, the displacement sensor 6 is subjected to zero reset, and then a preset static stress level is reached through application by the static actuators 21 in the $\sigma_1$ and $\sigma_2$ principle stress loading directions and remains constant. A time-dependent dynamic disturbance stress is applied by the dynamic actuators 31 in the static stress level, and parameters such as a disturbance direction, a disturbance frequency, a disturbance amplitude, a dynamic and static switching interval and a single-stage disturbance duration are determined by a time-dependent dynamic disturbance intelligent control center to control the disturbance stress application mode. The stress and strain situation of the rock test sample 13 is monitored in combination with the force-measuring sensor 5 and the displacement sensor 6, and the sampling interval of the displacement sensor 6 is automatically changed in combination with the intelligent filtering function. After the stress level disturbance stress is applied, the rock test sample 13 is not damaged, the static stress level is loaded to a second stage by the static actuators 21, and the disturbance stress application process is repeated. After the above steps are repeated for several times, the rock test sample 13 is ruptured instantly before being damaged. At this time, the acoustic emission receiver 7 sends a warning before damaging to the computer, automatically changes the sampling interval and identifies the instantaneous damage of the stress and strain level before damage the rupture situation. In the whole time-dependent dynamic disturbance process, the time-dependent dynamic disturbance intelligent control center controls the time-dependent dynamic disturbance process test for the deep-buried surrounding rock through the collaborative cooperation of intelligent power consumption control, an electro-hydraulic servo actuator and a radiating system. Test data will be exported by the computer and transferred to experimenters. Information includes stress and stress in the $\sigma_1$, $\sigma_2$ and $\sigma_3$ principle stress loading directions and rupture information, a test sample disturbance duration, a total test duration and other data.

What is claimed is:

1. A true triaxial time-dependent disturbance test device for a deep-buried hard rock, comprising: a test sample basic platform, wherein the test sample basic platform is provided with a hydrostatic pressure chamber, the hydrostatic pressure chamber forms a closed cavity structure by a pressure chamber top cover, a pressure chamber side wall and a pressure chamber bottom, and a flexible static load loading assembly, a test sample placing platform and an interlocking rigid clamp assembly are arranged in the hydrostatic pressure chamber;

wherein the flexible static load loading assembly applies a $\sigma_3$-direction flexible static load to a rock test sample, and is capable of applying a confining pressure type static load to the rock test sample during work; a rigid loading system is arranged outside the test sample basic platform, and the rigid loading system comprises two rigid static load loading assemblies and two rigid dynamic load loading assemblies, the rigid static load loading assemblies comprise a first rigid static load loading assembly and a second rigid static load loading assembly, and the rigid dynamic load loading assemblies comprise a first rigid dynamic load loading assembly and a second rigid dynamic load loading assembly; the rigid static load loading assemblies comprise static actuators, and the rigid dynamic load loading assemblies comprise dynamic actuators; the first rigid static load loading assembly is arranged in a $\sigma_1$ principle stress loading direction and applies a $\sigma_1$-direction static load to the rock test sample, the pressure chamber side wall is provided with a first reacting force support in the $\sigma_1$ principle stress loading direction, and the first reacting force support provides a reacting force of the $\sigma_1$-direction static load; the second rigid static load loading assembly is arranged in a $\sigma_2$ principle stress loading direction and applies a $\sigma_2$-direction static load to the rock test sample, the pressure chamber top cover is provided with a second reacting force support in the $\sigma_2$ principle stress loading direction, and the second reacting force support provides a reacting force of the $\sigma_2$-direction static load; the first rigid dynamic load loading assembly is arranged on a side opposite to the second rigid static load loading assembly and applies a $\sigma_2$-direction disturbance stress to the rock test sample; and the second rigid dynamic load loading assembly is arranged on a side opposite to the first rigid static load loading assembly and applies a $\sigma_1$-direction disturbance stress to the rock test sample;

wherein the device further comprises an intelligent information control and rupture sensing system having a closed-loop servo control working mode, and the intelligent information control and rupture sensing system comprises a $\sigma_1$ system, a $\sigma_2$ system, a $\sigma_3$ system and a time-dependent dynamic disturbance intelligent control center;

wherein the $\sigma_1$ system is provided with a first disturbance mode controller, and monitors and controls the static actuators and the dynamic actuators in the $\sigma_1$ principle stress loading direction; the $\sigma_2$ system is provided with a second disturbance mode controller, and monitors and controls the static actuators and the dynamic actuators in the $\sigma_2$ principle stress loading direction; the $\sigma_3$ system is provided with a third disturbance mode controller, and monitors and controls the flexible static load loading assembly in a $\sigma_3$ principle stress loading direction; the first disturbance mode controller, the second disturbance mode controller and the third disturbance mode controller are capable of monitoring an oil temperature and a power consumption of a servo oil source device and selecting a disturbance mode according to the oil temperature and the power consumption of the servo oil source device, is capable of applying a disturbance stress in a long-dynamic rheological test, and is also capable of performing scram braking on a disturbance loading control of a warning temperature.

2. The true triaxial time-dependent dynamic disturbance test device for the deep-buried hard rock according to claim 1, wherein the interlocking rigid clamp assembly comprises four test sample clamps, the test sample clamps comprises a first test sample clamp, a second test sample clamp, a third test sample clamp and a fourth test sample clamp, the first test sample clamp and the third test sample clamp are arranged oppositely on two sides of the rock test sample in the $\sigma_1$ principle stress loading direction, the second test sample clamp and the fourth test sample clamp are arranged oppositely on two sides of the rock test sample in the $\sigma_2$ principle stress loading direction, and the four test sample clamps are mutually slidingly connected in an interlocking manner; the pressure chamber side wall is provided with a first loading piston at a position corresponding to the first test sample clamp, the first loading piston is embedded into the pressure chamber side wall and slidingly connected, and the first loading piston is in contact with the first test sample clamp; the pressure chamber bottom is provided with a second loading piston at a position corresponding to the fourth test sample clamp, the second loading piston is embedded into the pressure chamber bottom and slidingly connected, and the second loading piston is in contact with the fourth test sample clamp; the pressure chamber side wall is fixedly provided with the first reacting force support at a position corresponding to the third test sample clamp, the first reacting force support is fixedly connected to the pressure chamber side wall, and the first reacting force support is in contact with the third test sample clamp; and the pressure chamber top cover is fixedly provided with the second reacting force support at a position corresponding to the second test sample clamp, the second reacting force support is fixedly connected to the pressure chamber top cover, and the second reacting force support is in contact with the second test sample clamp.

3. The true triaxial time-dependent dynamic disturbance test device for the deep-buried hard rock according to claim 2, wherein the rigid dynamic load loading assemblies further comprise dynamic self-balancing pistons, the third test sample clamp and the first reacting force support are provided with disturbance holes in the $\sigma_1$ principle stress loading direction, the second test sample clamp and the second reacting force support are provided with disturbance holes in the $\sigma_2$ principle stress loading direction, disturbance rods are arranged in the disturbance holes, the dynamic actuators, the dynamic self-balancing pistons and the disturbance rods are sequentially in contact with each other, and when the dynamic actuators work, the dynamic actuators apply $\sigma_1$-direction and $\sigma_2$-direction point disturbances to the rock test sample through the disturbance rods.

4. The true triaxial time-dependent dynamic disturbance test device for the deep-buried hard rock according to claim 3, wherein the rigid static load loading assemblies further comprise static self-balancing pistons, the first rigid static load loading assembly is in contact with the first loading piston, and the $\sigma_1$-direction static load is applied to the rock test sample sequentially through the first loading piston and the first test sample clamp; and the second rigid static load loading assembly is in contact with the second loading piston, and the $\sigma_2$-direction static load is applied to the rock test sample sequentially through the second loading piston and the fourth test sample clamp.

5. The true triaxial time-dependent dynamic disturbance test device for the deep-buried hard rock according to claim 2, wherein the four test sample clamps are mutually slidingly connected in an interlocking manner, and mutual extrusion of the test sample clamps is capable of being avoided when rigid loading is applied.

6. The true triaxial time-dependent dynamic disturbance test device for the deep-buried hard rock according to claim 4, wherein the interlocking rigid clamp assembly is further provided with deformation sensors and deformation sensor supports, the deformation sensors comprise a first deformation sensor, a second deformation sensor and a third deformation sensor, the deformation sensor supports comprise a first deformation sensor support, a second deformation sensor support and a third deformation sensor support, the first deformation sensor is arranged in the first test sample clamp, the first deformation sensor support is arranged in the third test sample clamp, the second deformation sensor is arranged in the fourth test sample clamp, the second deformation sensor support is arranged in the second test sample clamp, the third deformation sensor and the third deformation sensor support are arranged in a $\sigma_3$ principle stress loading direction, and each of the first deformation sensor and the second deformation sensor in $\sigma_1$ and $\sigma_2$ principle stress loading directions comprises a contact needle, a disk spring telescopic rod and an LVDT sensor main body, and is a sliding orthogonal deformation LVDT sensor measurement structure; the third deformation sensor in the $\sigma_3$ principle stress loading direction comprises a metal rod, a positioning block and an LVDT sensor, and is a fixed double-span beam LVDT sensor measurement structure.

7. The true triaxial time-dependent dynamic disturbance test device for the deep-buried hard rock according to claim 6, wherein the computer includes a large-capacity storage function, a test process intelligent switching sampling spacing function, disturbance load maintenance intelligent switching, a data intelligent filtering function and a rheological test process recording function; wherein the large-capacity storage function provides a storage space for long-time-dependent dynamic disturbance data; the test process intelligent switching sampling spacing function is capable of reducing the acquisition of useless data; the data intelligent filtering function is capable of filtering meaningless disturbance stress records in a disturbance rheological process.

8. The true triaxial time-dependent dynamic disturbance test device for the deep-buried hard rock according to claim 3, further comprising a rigid loading system framework, wherein the first rigid static load loading assembly and the second rigid dynamic load loading assembly are connected to the test sample basic platform through the rigid loading system framework, the rigid loading system framework is sleeved outside the test sample basic platform and is slidingly connected to the test sample basic platform, and a hydraulic lifting mechanism is arranged at a lower end of the test sample basic platform; the hydrostatic pressure chamber is of semi-closed cavity structure, and the hydrostatic pressure chamber is in an open state after the test sample basic platform descends; and after the test sample basic platform ascends, the rigid loading system framework closes the hydrostatic pressure chamber, the second rigid dynamic load loading assembly is in contact with the disturbance rods, and the first static load loading assembly is in contact with the first loading piston.

9. The true triaxial time-dependent dynamic disturbance test device for a deep-buried hard rock according to claim 4, wherein the static actuators and the dynamic actuators are connected to travel-measuring sensors.

* * * * *